United States Patent
Paez Prosper et al.

(10) Patent No.: US 8,815,846 B2
(45) Date of Patent: Aug. 26, 2014

(54) FAMILY OF ANTICHAGASICS DERIVED FROM IMIDAZO[4,5-C][1,2,6]THIADIAZINE 2,2-DIOXIDE

(75) Inventors: Juan Antonio Paez Prosper, Madrid (ES); Nuria Eugenia Campillo Martín, Madrid (ES); Ángela Guerra Álvarez, Madrid (ES); Maria Mercedes González Hormaizteguy, Montevideo (UY); Hugo Cerecetto Meyer, Montevideo (UY)

(73) Assignees: Universidad de la Republica de Uruguay, Mataojo Montevideo (UY); Consejo Superior de Investigaciones Cientificas, Madrid (ES)

( * ) Notice: Subject to any disclaimer, the term of this patent is extended or adjusted under 35 U.S.C. 154(b) by 528 days.

(21) Appl. No.: 13/146,259

(22) PCT Filed: Jan. 26, 2010

(86) PCT No.: PCT/ES2010/070042
§ 371 (c)(1),
(2), (4) Date: Oct. 31, 2011

(87) PCT Pub. No.: WO2010/086481
PCT Pub. Date: Aug. 5, 2010

(65) Prior Publication Data
US 2012/0035160 A1    Feb. 9, 2012

(30) Foreign Application Priority Data
Jan. 27, 2009 (ES) .................................. 200900225

(51) Int. Cl.
*A61K 31/549* (2006.01)
*C07D 285/16* (2006.01)
*A61K 31/433* (2006.01)

(52) U.S. Cl.
CPC .................................... *A61K 31/433* (2013.01)
USPC ....................................................... 514/222.8

(58) Field of Classification Search
USPC ....................................................... 514/222.8
See application file for complete search history.

(56) References Cited

PUBLICATIONS

Herrero et al. "2,2Dioxidos de 4-amino-pirazino {2,3-c]-1,2,6-tiadiazina 6,7-diaril sustituidos: una nueva serie de antihelminticos", An. Real Acad. Farm. 1989, 55: 451-459.
Martinez et al. "Imidazothiadiazine Dioxides: Synthesis and Antiviral Activity" Bioorganic & Medicinal Chemistry 7 (1999) 1617-1623Elsevier Science Ltd.
Coro et al. "Synthesis and antiprotozoan evaluation of new alkyl-linked bis(2-thioxo-[1,3,5]thiadiazinan-3-yl) carboxylic acids" Bioorganic & Medicinal Chemistry 13 (2005) 3413-3421.
Muelas et al. "New thiadiazine derivatives with activity against *Trypanosoma cruzi* amastigotes" Folia Parasitologica 48: 105-108, 2001.
International Search Report dated Dec. 5, 2010 for international application No. PCT/ES2010/070042.

*Primary Examiner* — San-Ming Hui
(74) *Attorney, Agent, or Firm* — Gardner Groff Greenwald & Villanueva, P.C.

(57) ABSTRACT

Compounds derived from imidazo[4,5-c][1,2,6]thiadiazine 2,2-dioxides, for use as a drug or pharmaceutical composition for treatment of parasitic diseases, preferably of diseases caused by parasites of the *Trypanosoma* genus, and more preferably for treatment of the Chagas disease. Furthermore, the invention also relates to the pharmaceutical compositions comprising said compounds.

20 Claims, No Drawings

FAMILY OF ANTICHAGASICS DERIVED FROM IMIDAZO[4,5-C][1,2,6]THIADIAZINE 2,2-DIOXIDE

IN THE CROSS-REFERENCE TO RELATED APPLICATIONS

This application claims priority to Spanish Application No. P200900225, filed Jan. 27, 2009, which is hereby incorporated by reference in its entirety for all purposes.

The present invention relates to the use of compounds derived from imidazo[4,5-c][1,2,6]thiadiazine 2,2-dioxides with antichagasic properties that modify or module the activity of cruzipain, directly or indirectly, and may behave as inhibitors thereof, depending on the substituents of the heterocyclic system. Therefore, the invention is included within the pharmaceutical sector.

PRIOR ART

Chagas disease, also called Tripanosomiasis Americana is a parasitic disease caused by a flagellated protozoan called *Trypanosoma cruzi*. This parasite is transmitted to the vertebrate hosts by a hematophage insect, *Triatoma infestans*, known as conenose or bedbug. Chagas disease can also be transmitted through blood transfusions from mothers to children during pregnancy, or with less frequency, through organ transplants or contaminated food. The parasite is reproduced in the internal tissues and causes problems in the heart, the oesophagus, the colon and the nervous system.

This disease is a parasitic endemic disease affecting around 18 million people in Latin America, extending from the south of the United States to Argentina and Chile. There is no vaccine against Chagas disease and the people affected can be reinfected after receiving pharmacological treatment.

The only two drugs marketed to date for treatment of this disease are Nifurtimox® (Nfx; (4-([5 nitrofurfurylidene]-amino)-3-methylthiomorpholine-1,1-dioxide) and Benznidazole® (Bnz, N-benzyl-2-nitro-1-imidazole acetamide), although there are problems of availability in some countries in South America. Although both Nfx and Bnz have been used in the treatment of Chagas disease since their introduction in the market (Nfx in 1965 and Bnz in 1971), the knowledge of their mechanism of action is not completely clarified.

These drugs have great drawbacks, since although they are effective in the blood form of the *T. Cruzi* parasite, they have low efficacy in the intracellular form. Likewise, they have highly toxicity which makes their use unsuitable in many situations such as pregnancy, and hepatic and renal insufficiency. Furthermore, it is necessary to consider the fact of the parasite's capacity to develop resistance to these drugs. Therefore, the development is necessary of new antichagasic drugs for treatment of Chagas disease.

There are different strategies in the search for new antichagasic drugs as well as very different structures from a chemical standpoint which are being studied for a better treatment of Chagas disease (Cerecetto, H, Gonzalez, M. Current Topics in Medicinal Chemistry, 2002, 2(11): 1187-1213. Cerecetto H, Gonzalez M. *Mini Rev. Med. Chem.* 2008, 8(13), 1355-83).

One of the lines of research on the increase arising as a consequence of the studies on biochemistry and metabolism of the *Trypanosoma cruzi* is that relating to cruzipain inhibitors. This enzyme also known as cruzipain (gp 57/51) is a cistein-protease responsible for proteolytic activity and, therefore, its inhibitors represent an interesting approach for treatment of Chagas disease (Roush, W. R., Cheng, J., Knapp-Reed, B., Alvarez-Hernandez, A., McKerrow, J. H., Hansell, E. and Engel, J. C. *Bioorg Med Chem Lett,* 2001, 11, 2759-62). Different structures, both of free cruzipain and forming complexes with different inhibitors, have been crystallized, which has made it possible to determine the corresponding three-dimensional structures by x-ray. (Eakin, A. E., McGrath, M. E., McKerrow, J. H., Fletterick, R. J. and Craik, C. S. *J Biol Chem,* 1993, 268, 6115-8; Huang, L., Brinen, L. S. and Ellman, J. A. *Bioorg Med Chem,* 2003, 11, 21-9; McGrath, M. E., Eakin, A. E., Engel, J. C., McKerrow, J. H., Craik, C. S. and Fletterick, R. J., *J Mol Biol,* 1995, 247, 251-9). The derivatives described as antichagasic drugs are highly varied from a chemical standpoint and include various heterocyclic compounds.

DESCRIPTION OF THE INVENTION

The present invention provides derivatives of imidazo[4,5-c][1,2,6]thiadiazine 2,2-dioxide with antichagasic properties. In other words, these compounds inhibit the growth of *Trypanosoma cruzi* in dose-dependent form with inhibitory concentrations ($IC_{50}$) in the order of 20 micromolar or are capable of inhibiting cruzipain. in vitro assays were performed on these compounds, studying the effects thereof on the growth of the epimastigote form of the Tulahuen 2 strain of *Trypanosoma cruzi* (see examples). To verify the selectivity towards the parasite cells, the non-specific cytotoxicity was studied of the most relevant compounds in mammal cells, J774 murine marcrophages. Furthermore, the capacity of this family of antichagasics derived from imidazo[4,5-c][1,2,6]thiadiazine 2,2-dioxide was assayed of inhibiting in vitro cruzipain, a protease cysteine present in all stages of the parasite.

In this way, a first aspect of the present invention relates to the compounds of general formula (I) or an isomer, pharmaceutically acceptable salt and/or solvate thereof (hereinafter compounds of the invention) for their use as a drug or pharmaceutical composition,

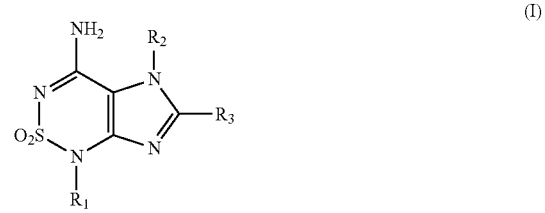

(I)

wherein:
$R_1$ and $R_2$, are the same or different, and are selected from the list comprising hydrogen, alkyl ($C_1$-$C_6$), cycloalkyl, heterocycle, aryl or aralkyl; and $R_3$ is selected from the list comprising, hydrogen, alkyl ($C_1$-$C_6$), cycloalkyl, heterocycle, aryl or aralkyl.

The term "alkyl" relates in the present invention a linear or branched aliphatic chains, which have from 1 to 6 carbon atoms, for example, methyl, ethyl, n-propyl, i-propyl, n-butyl, tert-butyl, sec-butyl, n-pentyl, n-hexyl. Preferably the alkyl group has between 1 and 3 carbon atoms. The alkyl groups may be optionally substituted by one or more substituents such as halogen, hydroxyl, azide, aryl carboxyl acid, hydroxyl, amine, amide, ester, carboxylic, ether, thiol, acylamine or carboxamide, which in turn may optionally be substituted.

The term "aryl" relates in the present invention to an aromatic carbocyclic chain, which has from 6 to 18 carbon atoms, and can be a single or multiple ring, in this last case with separated and/or condensed rings. A non-limiting example of aryl is a phenyl, naphthyl, indenyl group, etc. . . . Preferably the aryl group is a phenyl, wherein the phenyl group may contain 1 or more substituents of the group formed by alkyl, hydroxy, nitro, amine or halogen. Preferably a halogen and more preferably substituted by at least one chlorine or fluorine atom.

The term "aralkyl" relates, in the present invention, to an aliphatic chain wherein at least one of the hydrogens has been substituted by an aryl group, with the previous senses. Such as, for example, but without being limited to, a benzyl or phenethyl group. These aralkyl groups may, in turn, be optionally substituted by an alkyl, hydroxy, nitro, amine or halogen group. Preferably a halogen and more preferably substituted at least by one chlorine or fluorine atom.

"The term "cycloalkyl" relates to a stable monocyclic or bicyclic radical of 3 to 10 members that is saturated or partially saturated, and which only consists of carbon and hydrogen atoms, such as cyclopentyl, cyclohexyl or adamantyl.

The term "heterocycle" relates, in the present invention, to a carbocyclic chain radical and which consists of carbon atoms and of at least one heteroatom with 1 to 3 heteroatoms selected from the group consisting of nitrogen, oxygen or sulphur. This carbocyclic chain may be unsaturated, saturated or partially saturated. When the carbocyclic chain is saturated, the radical relates to a cycloalkyl group, as defined above, with at least one heteroatom in its chain selected from nitrogen, oxygen and/or sulphur. An example of this type of groups, but without limitation, is tetrahydrofuryl. When the chain is unsaturated or partially saturated, it is called heteroaryl.

The term "heteroaryl" relates in the present invention to an aromatic carbocyclic chain, which has from 6 to 18 carbon atoms, and can be a single or multiple ring, in this last case with separated and/or condensed rings, with 1 to 3 heteroatoms selected from the group consisting of nitrogen, oxygen and/or sulphur. A non-limiting example of heteroaryl is thienyl, furyl, pyrrolidinyl, pyrazolinyl, pyridinyl, piperidinyl or piperazinyl. The heteroaryl group, and the heterocycle group in general, may contain 1 or more substituents of the group formed by alkyl, hydroxy, nitro, amine or halogen. Preferably a substituted nitro or amine.

In a preferred embodiment of the compounds of the invention, $R_1$ and/or $R_2$ are hydrogen, methyl, benzyl or substituted benzyl, preferably benzyl substituted by a halogen, more preferably by a fluorine or chlorine atom.

In another preferred embodiment of the compounds of the invention, $R_3$ is a phenyl, substituted phenyl, cycloalkyl ($C_5$-$C_6$), benzyl, substituted benzyl, phenethyl, substituted phenethyl, alkyl ($C_1$-$C_3$) or a heterocycle. The substituted phenyl benzyl or phenethyl group is preferably substituted by a halogen, more preferably by a fluorine or chlorine atom. The heterocycle is preferably pyridyl, thienyl, furyl or tetrahydrofuryl.

In a more preferred embodiment of the use of the compounds of the invention, these compounds are selected from the list comprising:
4-amino-6-benzyl-1H,5H-imidazo[4,5-c][1,2,6]thiadiazine 2,2-dioxide,
4-amino-6-(5-nitro-2-furyl)-1H,5H-imidazo[4,5-c][1,2,6] thiadiazine 2,2-dioxide,
4-amino-6-(3-pyridyl)-1H,5H-imidazo[4,5-c][1,2,6]thiadiazine 2,2-dioxide,
4-amino-6-(2-fluorophenyl)-1H,5H-imidazo[4,5-c][1,2,6] thiadiazine 2,2-dioxide,
4-amino-6-(3-thienyl)-1H,5H-imidazo[4,5-c][1,2,6]thiadiazine 2,2-dioxide,
4-amino-6-(4-dimethylaminophenyl)-1H,5H-imidazo[4,5-c][1,2,6]thiadiazine 2,2-dioxide,
4-amino-6-cyclopentyl-1H,5H-imidazo[4,5-c][1,2,6]thiadiazine 2,2-dioxide,
4-amino-6-cyclohexyl-1H,5H-imidazo[4,5-c][1,2,6]thiadiazine 2,2-dioxide,
4-amino-6-(3-tetrahydrofuryl)-1H,5H-imidazo[4,5-c][1,2,6] thiadiazine 2,2-dioxide,
4-amino-6-ethyl-1H,5H-imidazo[4,5-c][1,2,6]thiadiazine 2,2-dioxide,
4-amino-6-phenethyl-1H,5H-imidazo[4,5-c][1,2,6]thiadiazine 2,2-dioxide,
4-amino-1-(4-chlorobenzyl)-6-(2-fluorophenyl)-5H-imidazo[4,5-c][1,2,6]thiadiazine 2,2-dioxide,
4-amino-6-phenyl-1-methyl-5H-imidazo[4,5-c][1,2,6]thiadiazine 2,2-dioxide,
4-amino-1,5-dibenzyl-6-cyclohexylimidazo[4,5-c][1,2,6] thiadiazine 2,2-dioxide,
4-amino-1,5-dibenzyl-6-phenylimidazo[4,5-c][1,2,6]thiadiazine 2,2-dioxide,
4-amino-1,5-dibenzyl-6-cyclohexylimidazo[4,5-c][1,2,6] thiadiazine 2,2-dioxide,
4-amino-6-cyclohexyl-1-(4-chlorobenzyl)-5H-imidazo[4,5-c][1,2,6]thiadiazine 2,2-dioxide,
4-amino-1,5-bis(4-chlorobenzyl)-6-cyclohexylimidazo[4,5-c][1,2,6]thiadiazine 2,2-dioxide,
4-amino-1-(4-chlorobenzyl)-6-(2-fluorophenyl)-5-(2-naphthyl)imidazo[4,5-c][1,2,6]thiadiazine 2,2-dioxide,
4-amino-6-phenyl-1H,5H-imidazo[4,5-c][1,2,6]thiadiazine 2,2-dioxide,
4-amino-6-methyl-1H,5H-imidazo[4,5-c][1,2,6]thiadiazine 2,2-dioxide,
4-amino-1-benzyl-6-phenyl-5H-imidazo[4,5-c][1,2,6]thiadiazine 2,2-dioxide,
4-amino-1-benzyl-5-(4-chlorobenzyl)-6-phenylimidazo[4,5-c][1,2,6]thiadiazine 2,2-dioxide or
4-amino-6-cyclohexyl-5-(4-chlorobenzyl)-1-benzylimidazo[4,5-c][1,2,6]thiadiazine 2,2-dioxide Another aspect of the present invention relates to the compounds of general formula (I) for their use in the preparation of a drug or pharmaceutical composition for treatment of parasitic diseases, in general, of diseases produced by parasites of the Trypanosoma genus, such as, for example, Chagas disease, and in particular, diseases associated with the activity of cruzipain and/or which may benefit from the biological activities shown by the products described in the present invention, or a pharmaceutically acceptable salt, derivative, prodrugs or solvate thereof.

The compounds of the present invention represented by formula (I) may include isomers, including optical isomers or enantiomers, depending on the presence of chiral centres. The individual isomers, enantiomers or diastereoisomers and the mixtures thereof fall within the scope of the present invention. The individual enantiomers or diastereoisomers, as well as their mixtures, may be separated by conventional techniques.

As used here, the term "derivative" includes both pharmaceutically acceptable compounds, i.e. derived from the compound of formula (I) which can be used in the preparation of a drug, and pharmaceutically unacceptable derivatives since they may be useful in the preparation of pharmaceutically acceptable derivatives. The nature of the pharmaceutically acceptable derivative is not critical, provided it is pharmaceutically acceptable.

Likewise, within the scope of this invention are the prodrugs of the compounds of formula (I). The term "prodrug" as used here includes any compound derived from a compound of formula (I), for example, esters, including carboxylic acid esters, amino acid esters, phosphate esters, sulfonate esters of metal salts, etc., carbamates, amides, etc., which, when administered to an individual, is capable of providing, directly or indirectly, said compound of formula (I) in said individual. Advantageously, said derivative is a compound which increases the bioavailability of the compound of formula (I) when administered to an individual or which enhances the release of the compound of formula (I) in a biological compartment. The nature of said derivative is not critical whenever it can be administered to an individual and provides the compound of formula (I) in a biological compartment of an individual. The preparation of said prodrug can be carried out by conventional methods known by persons skilled in the art.

The compounds of the invention may be in crystalline form as free compounds or as solvates and the aim is that both forms are within the scope of the present invention. In this sense, the term "solvate", as used here, includes both pharmaceutically acceptable solvates, i.e. solvates of the compound of formula (I) which may be used in the preparation of a drug, and pharmaceutically unacceptable solvates, which may be useful in the preparation of pharmaceutically acceptable solvates or salts. The nature of the pharmaceutically acceptable solvate is not critical provided that it is pharmaceutically acceptable. The solvates can be obtained by conventional solvation methods known by persons skilled in the art.

For their application in therapy, the compounds of formula (I), their isomers, salts, prodrugs or solvates, are found, preferably, in a pharmaceutically acceptable or substantially pure form, i.e. which has a pharmaceutically acceptable purity level excluding the normal pharmaceutical additives such as diluents and carriers, and not including material considered toxic at normal dosage levels. The purity levels for the active principle are preferably over 50%, more preferably over 70%, more preferably over 90%. In a preferred embodiment, they are over 95% of the compound of formula (I), or of its salts, solvates or prodrugs.

The compounds of the present invention of formula (I) may be obtained or produced by a chemical synthetic route or obtained from a natural material of different origin.

In a preferred embodiment of the present invention the process of obtainment of the compounds of the invention of formula (I) or an isomer, pharmaceutically acceptable salt and/or solvate thereof, comprise the following reaction steps, according to diagram 1:

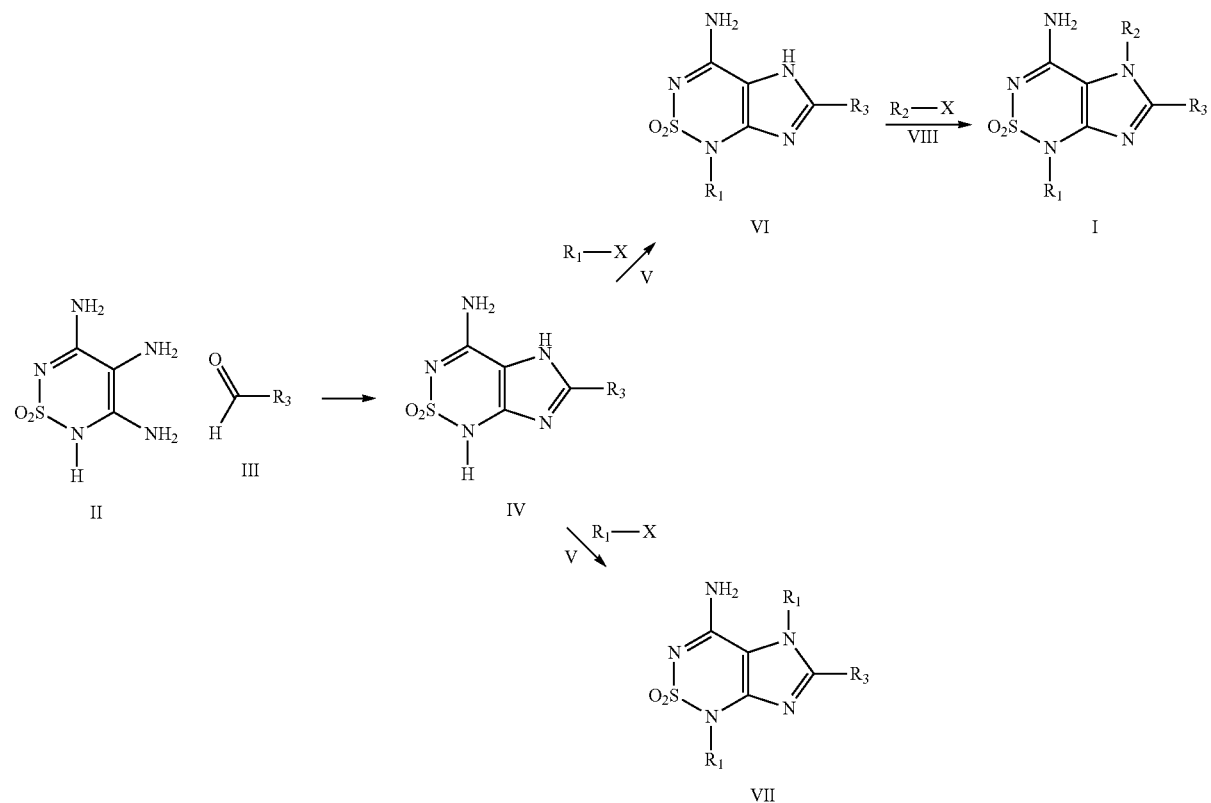

Diagram 1

The synthetic route described in diagram 1 comprises different stages:

The preparation of the N-1H, N-5H derivatives of general formula IV consists of the reaction of the 3,4,5-triamino-2H-1,2,6-thiadiazine 1,1-dioxide of formula (II) with aldehydes of general formula (III), wherein $R_3$ is previously described.

The 3,4,5-triamino-2H-1,2,6-thiadiazine 1,1-dioxide was prepared, according to a process described in two reaction stages, from 3,5-diamino-4H-1,2,6-thiadiazine 1,1-dioxide (Ochoa, C. and Stud, M., 1978, *J. Heterocycl. Chem.*, 15, 221-224).

The preparation of the substituted N-1 derivatives of general formula (VI) consists of the reaction of the 4-amino-1H, 5H-imidazo[4,5-c][1,2,6]thiadiazine 2,2-dioxide of structure (IV) with halides of general formula (V), wherein $R_1$ is previously described.

Finally, preparation of the disubstituted N-1, N-5 derivatives may be performed by two different processes.

The first consists of the reaction of the derivatives of 4-amino-1H,5H-imidazo[4,5-c][1,2,6]thiadiazine 2,2-dioxide of general formula (IV) with halides of general formula (V), to give the compounds of general formula (VII), wherein $R_2$ is equal to $R_1$ in the compound of general formula (I) and $R_1$ and $R_3$ are previously defined.

The second process consists of the preparation of compounds of general formula (I) from the substituted N-1 derivatives of general formula (VI), by reaction with the corresponding halides of general formula (VIII), wherein $R_1$, $R_2$ and $R_3$ are previously defined.

A further aspect of the present invention relates to a pharmaceutical composition useful for the treatment of parasitic diseases, hereinafter pharmaceutical composition of the invention, comprising a compound, in therapeutically effective quantity, of formula (I), or mixtures thereof, a pharmaceutically acceptable salt, prodrug, solvate or stereoisomer thereof together with a carrier, adjuvant or pharmaceutically acceptable vehicle, for administration to a patient.

The pharmaceutically acceptable adjuvants and vehicles that may be used in said compositions are the adjuvants and vehicles known by persons skilled in the art and typically used to prepare therapeutic compositions.

In the sense used in this description, the expression "therapeutically effective quantity" relates to the quantity of the agent or compound capable of developing the therapeutic action determined by their pharmacological properties, calculated to produce the desired effect and, in general, it will be determined, among other causes, by the typical characteristics of the compounds, including the age, condition of the patient, the severity of the alteration or disorder and the route and frequency of administration.

The compounds described in the present invention, their pharmaceutically acceptable salts, prodrugs and/or solvates as well as the use of pharmaceutical compounds that contain them may be used together with other additional drugs, or active principles, to provide a combination therapy. Said additional drugs may form part of the same pharmaceutical composition or, alternatively, they may be provided in the form of a separate composition for their simultaneous administration or not to that of the pharmaceutical composition comprising a compound of formula (I) or a pharmaceutically acceptable prodrug, solvate, derivative or a salt thereof.

Said therapeutic composition can be prepared in the form of a solid form or aqueous suspension, in a pharmaceutically acceptable diluent. The therapeutic composition provided by the present invention may be administered by any appropriate administration route; to this end, said composition will be formulated in the suitable pharmaceutical form for the selected administration route. In a particular embodiment, the administration of the therapeutic composition provided by this invention is performed by oral, topical rectal or parenteral route (including subcutaneous, intraperitoneal, intradermal, intravenous, etc.).

The use of the compounds of the invention is compatible with their use in protocols wherein the compounds of the formula (I), or their mixtures are used by themselves or in combinations with other treatments or any medical process.

Another aspect of the present invention relates to the compounds of formula:

4-amino-6-benzyl-1H,5H-imidazo[4,5-c][1,2,6]thiadiazine 2,2-dioxide,
4-amino-6-(2-fluorophenyl)-1H,5H-imidazo[4,5-c][1,2,6]thiadiazine 2,2-dioxide,
4-amino-6-(3-thienyl)-1H,5H-imidazo[4,5-c][1,2,6]thiadiazine 2,2-dioxide,
4-amino-6-(3-pyridyl)-1H,5H-imidazo[4,5-c][1,2,6]thiadiazine 2,2-dioxide,
4-amino-6-(4-dimethylaminophenyl)-1H,5H-imidazo[4,5-c][1,2,6]thiadiazine 2,2-dioxide,
4-amino-6-cyclopentyl-1H,5H-imidazo[4,5-c][1,2,6]thiadiazine 2,2-dioxide,
4-amino-6-cyclohexyl-1H,5H-imidazo[4,5-c][1,2,6]thiadiazine 2,2-dioxide,
4-amino-6-(3-tetrahydrofuryl)-1H,5H-imidazo[4,5-c][1,2,6]thiadiazine 2,2-dioxide,
4-amino-6-ethyl-1H,5H-imidazo[4,5-c][1,2,6]thiadiazine 2,2-dioxide,
4-amino-6-phenethyl-1H,5H-imidazo[4,5-c][1,2,6]thiadiazine 2,2-dioxide,
4-amino-1-(4-chlorobenzyl)-6-(2-fluorophenyl)-5H-imidazo[4,5-c][1,2,6]thiadiazine 2,2-dioxide,
4-amino-6-phenyl-1-methyl-5H-imidazo[4,5-c][1,2,6]thiadiazine 2,2-dioxide,
4-amino-1,5-dibenzyl-6-cyclohexylimidazo[4,5-c][1,2,6]thiadiazine 2,2-dioxide,
4-amino-1,5-dibenzyl-6-phenylimidazo[4,5-c][1,2,6]thiadiazine 2,2-dioxide,
4-amino-1,5-dibenzyl-6-cyclohexylimidazo[4,5-c][1,2,6]thiadiazine 2,2-dioxide,
4-amino-6-cyclohexyl-1-(4-chlorobenzyl)-5H-imidazo[4,5-c][1,2,6]thiadiazine 2,2-dioxide
4-amino-1,5-bis(4-chlorobenzyl)-6-cyclohexylimidazo[4,5-c][1,2,6]thiadiazine 2,2-dioxide,
4-amino-1-benzyl-5-(4-chlorobenzyl)-6-phenylimidazo[4,5-c][1,2,6]thiadiazine 2,2-dioxide or
4-amino-1-benzyl-6-cyclohexyl-5-(4-chlorobenzyl)imidazo[4,5-c][1,2,6]thiadiazine 2,2-dioxide.

Throughout the description and the claims the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Below, the invention will be illustrated with assays performed by the inventors, which reveals the specificity and efficacy of the compounds of the invention.

Example 1

General Obtainment Process of 4-amino-1H,5H-imidazo[4,5-c][1,2,6]thiadiazine 2,2-dioxides To a suspension of 3,4,5-triamino-2H-1,2,6-thiadiazine 1,1-dioxide in slightly acidic water (HAc glacial) add, under stirring and in small fractions, the corresponding aldehyde. After the reaction time, the solid formed is vacuum filtered, washed with the appropriate solvent and was purified by recrystallization. The reaction times, as well as the specific conditions and treatments are described individually for each compound.

Example 1a

Preparation and obtainment of 4-amino-6-cyclohexyl-1H,5H-imidazo[4,5-c][1,2,6]thiadiazine 2,2-dioxide. From 1.500 g (8.5 mmol) of 3,4,5-triamino-2H-1,2,6-thiadiazine 1,1-dioxide, 3.2 ml (25.5 mmol) of cyclohexanecarboxaldehyde, 30 ml of $H_2O$ and 4 ml of glacial acetic acid. Reaction time: 24 h. Washing with EtOH. Recrystallized from EtOH/$H_2O$ Yield: 1.047 g (46%) M.p.=263-265° C. $^1$H-NMR (400 MHz, DMSO-$d_6$) δ: 11.82, 11.00 (sa, 2H, NH); 7.42 (sa, 2H, $NH_2$); 2.67 (sa, 1H, 1'-H); 1.94-1.18 (m, 10H, 2'-H/3'-H/4'-H). $^{13}$C-NMR (100 MHz, DMSO-$d_6$) δ: 155.8 (C-4); 152.9 (C-7a); 150.4 (C-6); 101.2 (C-4a); 37.2 (C-1'); 30.9 (2C, C-2'); 25.4, 25.2 (3C, C-3'/C-4'). Anal. ($C_{10}H_{15}N_5O_2S$) % theoretical (% experimental) C, 44.60 (44.33); H, 5.61 (5.54); N, 26.00 (26.24); S, 11.91 (11.82). EM (ES+) m/z (int. rel.): 270 (100%) [M+H]. HPLC: MeCN/$H_2O$ 5:95, r.t. 5.80 min., 97%.

Example 1b

Preparation and obtainment of 4-amino-6-(3-tetrahydrofuryl)-1H,5H-imidazo[4,5-c][1,2,6]thiadiazine 2,2-dioxide. From 0.300 g (1.69 mmol) of 3,4,5-triamino-2H-1,2,6-thiadiazine 1,1-dioxide, 0.49 ml (2.54 mmol) of tetrahydrofuran-3-carboxaldehyde, 30 ml of $H_2O$ and 2 ml of glacial acetic acid. After this reaction time, the mixture was dried and the solid obtained was washed with hexane and vacuum filtered. Reaction time: 48 h. Washing with Hexane. Recrystallized from EtOH. Yield: 0.181 g (41.2%) M.p.=238-240° C. $^1$H-NMR (500 MHz, DMSO-$d_6$) δ: 11.97, 11.00 (sa, 2H, NH); 7.63-7.22 (sa, 2H, $NH_2$); 3.98-3.74 (m, 4H, 2'-H/4'-H); 3.54-3.45 (sa, 1H, 1'-H); 2.30-2.23 (m, 1H, $5_a$'-H); 2.12-2.05 (m, 1H, $5_b$'-H). $^{13}$C-NMR (125 MHz, DMSO-$d_6$) δ: 152.9 (2C, C-4/C-7a); 150.3 (C-6); 101.9 (C-4a); 71.2 (C-2'); 67.4 (C-4'); 38.3 (C-1'); 31.3 (C-5'). Anal. ($C_8H_{11}N_5O_3S$) % theoretical (% experimental) C, 37.35 (37.24); H, 4.31 (4.29); N, 27.22 (27.05); S, 12.46 (12.21). EM ($ES^+$) m/z (int. rel.): 258 (100%) [M+H]. HPLC: MeCN/$H_2O$ 5:95, r.t. 1.20/1.63 min. (1.6:1), 100% purity; MeCN/$H_2O$ 1:99, r.t. 1.23/2.42 min. (1.6:1), 100%.

Example 1c

Preparation and obtainment of 4-amino-6-phenethyl-1H,5H-imidazo[4,5-c][1,2,6]thiadiazine 2,2-dioxide. From 0.300 g (1.69 mmol) of 3,4,5-triamino-2H-1,2,6-thiadiazine 1,1-dioxide, 0.34 ml (2.54 mmol) of 3-phenylpropionaldehyde, 12 ml of $H_2O$ and 2 ml of glacial acetic acid. After this reaction time the crude reaction product was vacuum filtered and washed with hexane. Reaction time: 24 h. Washing with Hexane. Recrystallized from EtOH/$H_2O$. Yield: 0.369 g (74.9%) M.p.=190-192° C. $^1$H-NMR (300 MHz, DMSO-$d_6$) δ: 12.09, 11.96, 11.03 (sa, 2H, NH); 7.81, 7.66 (sa, 2H, $NH_2$); 7.27-7.17 (m, 5H, Ph); 2.99, 2.96 (2s, 4H, $CH_2CH_2$). $^{13}$C-NMR (125 MHz, DMSO-$d_6$) δ: 154.2 (C-7a); 152.7 (C-4); 150.5 (C-6); 140.5 (C-1'); 128.5 (2C, C-3'); 128.3 (2C, C-2'); 126.2 (C-4'); 101.5 (C-4a); 32.9 ($\underline{CH_2}CH_2Ph$); 29.9 ($CH_2\underline{CH_2}Ph$). Anal. ($C_{12}H_{13}N_5O_2S$) % theoretical (% experimental) C, 49.47 (49.38); H, 4.50 (4.38); N, 24.04 (23.89); S, 11.01 (10.85). EM ($ES^+$) m/z (int. rel.): 292 (100%) [M+H]. HPLC: MeCN/$H_2O$ 5:95, r.t. 6.72 min., 98%.

Example 2

General Obtainment Process of 4-amino-5H-imidazo[4,5-c][1,2,6]thiadiazine N-1 substituted 2,2-dioxides A suspension of the N(H) derivative in acetone and in the presence of triethylamine or potassium carbonate was heated under stirring and once the reflux was reached a quantity of potassium iodide and the corresponding alkylating agent were added. After observing the complete disappearance of the starting N(H) derivative, the solvent was vacuum eliminated and the mixture obtained was treated in each case for its purification. The conditions, solvents and specific media are detailed individually for each compound.

Example 2a

Preparation and obtainment of 4-amino-1-(4-chlorobenzyl)-6-(2-fluorophenyl)-5H-imidazo[4,5-c][1,2,6]thiadiazine 2,2-dioxide. From 0.500 g (1.78 mmol) of 4-amino-6-(2-fluorophenyl)-1H,5H-imidazo[4,5-c][1,2,6]thiadiazine 2,2-dioxide 1H,5H, 0.740 g (3.56 mmol) of benzyl bromide, 100 ml of acetone and 1 ml (7.12 mmol) of triethylamine. After the reaction time, the solvent was vacuum eliminated and the mixture obtained was recrystallized with an acetone/$H_2O$. Reaction time: 5 days Recrystallized from mixture: acetone/$H_2O$ mixture. Yield: 0.158 g (39%) M.p.=304-305° C. $^1$H-NMR (500 MHz, DMSO-$d_6$) δ: 12.47 (sa, 1H, NH); 8.21, 7.96 (sa, 2H, $NH_2$); 8.10 (t, 1H, 6'-H, J=7.0); 7.58-7.37 (m, or-FPh/p-ClPh); 5.02 (s, 2H, $CH_2$). $^{13}$C-NMR (125 MHz, DMSO-$d_6$) δ: 159.1 (d, C-2', J=250.0); 152.4 (C-4); 150.7 (C-7a); 143.4 (C-6); 136.5 (C-1"); 132.4 (d, C-4', J=8.2); 132.0 (C-4"); 129.8 (2C, C-2" or C-3") 129.8 (d, C-6', J=6.4); 128.2 (2C, C-2" or C-3"); 125.4 (C-5'); 116.5 (d, C-3', J=22.0); 116.2 (d, C-1', J=11.9); 103.7 (C-4a). Anal. ($C_{17}H_{13}ClFN_5O_2S_2$) % theoretical (% experimental) C, 50.31 (50.30); H, 3.23 (3.35); N, 17.26 (17.05); S, 7.90 (7.65). EM (ES+) m/z (int. rel.): 354 (100%) [M+H]. HPLC: MeCN/$H_2O$ 5:95, r.t. 13.90 min., 100%.

Example 2b

Preparation and obtainment of 4-amino-1,5-dibenzyl-6-cyclohexylimidazo[4,5-c][1,2,6]thiadiazine 2,2-dioxide. From 0.300 g (1.11 mmol) of 4-amino-6-(3-thienyl)-5H-imidazo[4,5-c][1,2,6]thiadiazine 2,2-dioxide, 0.7 ml (11.1 mmol) of methyl iodide, 40 ml of acetone and 0.30 ml (2.22 mmol) of triethylamine. After this reaction time the solvent was vacuum eliminated and acid $H_2O$ was added. The precipitate obtained was vacuum filtered and purified by column chromatography using $CH_2Cl_2$:MeOH (100:1) as eluent. Reaction time: 4 days. Yield: 0.197 g (63%). M.p.=305-308° C. $^1$H-NMR (400 MHz; DMSO-$d_6$) δ: 13.04 (sa, 1H, NH); 8.00-7.20 (sa, 2H, $NH_2$); 8.04 (dd, 2'-H, $J_{2'-H, 5'-H}$=1.2/$J_{2'-H, 4'-H}$=2.9); 7.70 (dd, 4'-H, $J_{2'-H, 4'-H}$=2.9/$J_{4'-H, 5'-H}$=5.0); 7.55 (dd, 5'-H, $J_{2'-H, 5'-H}$=1.2/$J_{4'-H, 5'-H}$=5.0). $^{13}$C-NMR (100 MHz; DMSO-$d_6$) δ: 153.7 (C-4); 149.4 (C-7a); 143.9 (C-6); 131.0 (C-1'); 128.6 (C-4'); 125.7 (C-5'); 125.5 (C-2'); 104.2 (C-4a). Anal. ($C_9H_9N_5O_2S_2$) % theoretical (% experimental) C, 38.15 (38.39); H, 3.20 (2.90); N, 24.72 (25.28); S, 22.63 (23.02). EM ($ES^+$) m/z (int. rel.): 284 (100%) [M+H]. HPLC: MeCN/$H_2O$ 5:95, r.t. 9.42 min., 100%.

Example 3

Preparation of 4-aminoimidazo[4,5-c][1,2,6]thiadiazine 2,2-dioxides substituted in N-1 and N-5

Method A: From 4-amino-1H,5H-imidazo[4,5-c][1,2,6]thiadiazine 2,2-dioxides

A suspension of the N(H) derivative in acetone and potassium carbonate was heated under stirring and once the reflux was reached a catalytic quantity of potassium iodide and the corresponding alkyl halide was added. After observing the complete disappearance of the starting N(H) derivative, the solvent was vacuum eliminated. Once the salts in acid aqueous medium have been eliminated, the crude reaction product was purified by column chromatography. Obtainment of mixture of mono N1-R and disubstituted N1-R/N5-R products.

Example 3a

Preparation and obtainment of 4-amino-1,5-dibenzyl-6-phenylimidazo[4,5-c][1,2,6]thiadiazine 2,2-dioxide. From 0.600 g (2.28 mmol) of 4-amino-6-phenyl-1H,5H-imidazo[4,5-c][1,2,6]thiadiazine 2,2-dioxide, 0.98 ml (7.98 mmol) of benzyl bromide, 50 ml of acetone and 0.398 g (2.85 mmol) of potassium carbonate. The crude product obtained was purified by $CH_2Cl_2$ compact column chromatography and using the mixture $CH_2Cl_2$:MeOH (100:1) as eluent. Reaction time: 5 days. Yield: 0.075 g (8%) M.p.=238-240° C. $^1$H-NMR (300 MHz, DMSO-$d_6$) δ: 8.0-7.0 (sa, 2H, $NH_2$); 7.63-7.60 (m, 2H, Ph); 7.54-7.50 (m, 3H, Ph); 7.39-7.20 (m, 10H, N1-Bn/N5-Bn); 5.53 (s, 2H, N5-$CH_2$Ph); 5.02 (s, 2H, N1-$CH_2$Ph). $^{13}$C-NMR (75 MHz, $CDCl_3$) δ: 153.7 (C-4); 152.8 (C-7a); 152.1 (C-6); 137.4 (C-1" or C-1'''); 136.2 (C-1" or C-1'''); 130.9 (C-1'); 129.6, 129.2, 129.1, 128.5, 128.4, 128.2, 127.9, 127.5 (11C, Ph/N1-Bn/N5-Bn); 125.9 (C-2'); 105.0 (C-4a). Anal. ($C_{24}H_{21}N_5O_2S$) % theoretical (% experimental) C, 64.99 (64.79); H, 4.77 (4.56); N, 15.79 (15.61); S, 7.23 (6.98). EM (ES$^+$) m/z (int. rel.): 444 (100%) [M+H]. HPLC: MeCN/$H_2O$ 20:80, r.t. 12.63 min., 100%.

Method B: From 4-amino-5H-imidazo[4,5-c][1,2,6]thiadiazine 2,2-dioxides N-1 substituted A suspension of the N(H) derivative in acetone and in the presence of potassium carbonate was heated under stirring and once the reflux was reached a catalytic quantity of potassium iodide and the corresponding alkylating agent were added. After observing the complete disappearance of the starting N(H) derivative, the solvent was vacuum eliminated and the mixture obtained is treated in each case for its purification. The specific conditions, solvents and solvents are detailed individually for each compound.

Example 3b

Preparation and obtainment of 4-amino-1-benzyl-5-(4-chlorobenzyl)-6-phenylimidazo[4,5-c][1,2,6]thiadiazine 2,2-dioxide. From 0.200 g (0.57 mmol) of 4-amino-1-benzyl-6-phenyl-5H-imidazo[4,5-c][1,2,6]thiadiazine 2,2-dioxide, 0.191 g (1.13 mmol) of p-chlorobenzyl bromide, 40 ml of acetone and 0.157 g (1.13 mmol) of potassium carbonate. The product was purified in $CH_2Cl_2$ compact column chromatography and using the mixture $CH_2Cl_2$:MeOH (200:1) as eluent. Reaction time: 5 days. Yield: 0.035 g (13%).
M.p.=245-247° C. $^1$H-NMR (500 MHz, $CDCl_3$) δ: 7.63-7.18 (m, 14$H_{arom}$); 5.24 (s, 2H, N1-$CH_2$Ph); 4.90 (s, 2H, N5-$CH_2$-(p-ClPh)). $^{13}$C-NMR (125 MHz, $CDCl_3$) δ: 154.3 (C-4); 153.5 (C-7a); 152.0 (C-6); 136.6 (C-1" or C-1'''); 135.5 (C-1" or C-1'''); 133.5 (C-4'''); 131.2 (C-1'); 130.6 (2$C_{arom}$); 129.1 (2$C_{arom}$), 129.0 (2$C_{arom}$), 129.0 (2$C_{arom}$), 128.4 (2$C_{arom}$), 127.7 (2$C_{arom}$), 126.8 (2$C_{arom}$); 105.4 (C-4a); 49.6 ($CH_2$Ph); 47.8 ($CH_2$-(p-ClPh)). Anal. ($C_{24}H_{21}N_5O_2S$) % theoretical (% experimental) C, 60.31 ( ); H, 4.22 ( ); N, 14.65 ( ); S, 6.71 ( ). EM (ES$^+$) m/z (int. rel.): 478 (100%) [M+H]. HPLC: MeCN/$H_2O$ 20:80, r.t. 13.58 min., 94%.

Example 4

The studies of the antichagasic activity were performed in vitro against *Trypanosoma cruzi*, on the epimastigote form of the Tulahuen 2 strains, (from the strains collection of the Biological Physicochemistry Laboratory, of the Institute of Biological Chemistry, of the Faculty of Science, University of the Republica Oriental of Uruguay, Uruguay). Said strains were cultured at 28° C. in an axenic medium (BHI-tryptose), complemented with 5% of fetal bovine serum. It started from culture cells of 5-7 days (exponential phase) which were inoculated with 50 mL fresh culture medium giving an initial concentration of $1 \times 10^6$ cells/mL. The growth of the parasite was followed during 11 days by culture absorbance measurements at 600 nm, proportional to the number of cells present.

Before inoculation, a pre-established quantity of each compound of the invention to test was incorporated in the medium, dissolved in DMSO (dimethylsulfoxide). The final concentration of DMSO in the culture medium never exceeded 0.4%, using a blank (absence of product or compound of the invention) with 0.4% DMSO. The compounds were incorporated in the culture medium at a final concentration of 25 μM and for those that were most active, the dose was progressively decreased to 1 nM. The percentage of inhibition (PI) of growth of the parasite was evaluated in comparison with the blank, using Nfx (Nifurtimox) as trypanosomicide reference drug. The growth PI was calculated as follows:

$$PI = \{1 - [(A_p - A_{op})/(A_c - A_{oc})]\} \times 100$$

where:

$A_p = A_{600\,nm}$ of the culture containing the product on day 5.

$A_{op} = A_{600\,nm}$ of the culture containing the product after addition of the culture (day 0).

$A_c = A_{600\,nm}$ of the blank on day 5.

$A_{oc} = A_{600\,nm}$ of the blank on day 0.

The $A_{600\,nm}$ taken on day 5 corresponds to the late exponential phase in the culture growth curve.

The determination of the $IC_{50}$ (half maximal inhibitory concentration) was performed following the growth of the parasite in the absence (control) and presence of increasing concentrations of the corresponding products. The absorbance was measured on day 5 and it was related to the control. The $IC_{50}$ (half maximal inhibitory concentration) is defined as the concentration of product required to give a PI of 50%; the lower this value is the higher the potency of the compounds.

Table 1 shows, as examples, $IC_{50}$ data of some of the imidazo[4,5-c][1,2,6]thiadiazine 2,2-dioxide derivatives claimed in the present invention. Nifurtimox and Benznidazole are included as reference drugs. The compounds have an excellent trypanosomicide activity in vitro. The potency, in some cases, being greater than that of the reference drugs.

TABLE 1

Anti-*T. cruzi* structures and activity of the Tulahuen 2 strain

| Compounds | IC$_{50}$ (μM) |
|---|---|
| Nifurtimox | 7.7 |
| 4-amino-6-(2-fluorophenyl)-imidazo-thiadiazine dioxide | 20.2 |
| 4-amino-6-(3-thienyl)-imidazo-thiadiazine dioxide | 22.2 |
| 4-amino-6-(4-dimethylaminophenyl)-imidazo-thiadiazine dioxide | 28.5 |
| 4-amino-6-cyclopentyl-imidazo-thiadiazine dioxide | 28.9 |
| 4-amino-6-benzyl-imidazo-thiadiazine dioxide | 16.2 |
| 4-amino-1-methyl-6-phenyl-imidazo-thiadiazine dioxide | 16.7 |
| 4-amino-1-methyl-6-(3-thienyl)-imidazo-thiadiazine dioxide | 26.2 |
| 4-amino-1,5-dibenzyl-6-phenyl-imidazo-thiadiazine dioxide | 4.5 |
| Benznidazole | 7.4 |
| 4-amino-6-cyclohexyl-imidazo-thiadiazine dioxide | 12.7 |
| 4-amino-6-(tetrahydrofuran-3-yl)-imidazo-thiadiazine dioxide | 20.3 |
| 4-amino-6-ethyl-imidazo-thiadiazine dioxide | 28.5 |
| 4-amino-6-(2-phenylethyl)-imidazo-thiadiazine dioxide | 11.5 |
| 4-amino-1-benzyl-6-phenyl-imidazo-thiadiazine dioxide | 29.5 |

TABLE 1-continued

Anti-*T. cruzi* structures and activity of the Tulahuen 2 strain

| Compounds | IC$_{50}$ (μM) |
|---|---|
| (structure: 4-amino imidazo-thiadiazine with 2-fluorophenyl and N-(4-chlorobenzyl)) | 7.0 |
| (structure: 4-amino imidazo-thiadiazine with cyclohexyl and N-benzyl, N-benzyl) | 28.7 |
| (structure: 4-amino imidazo-thiadiazine with phenyl and N-(4-chlorobenzyl), N-benzyl) | 10.0 |

[a] The assay is carried out in duplicate with an error of ±3%.

The non-specific cytotoxicity against J774 murine macrophages was assayed in the products that presented a percentage of growth inhibition of the epimastigote form of T. cruzi of the Tulahuen 2 strain, greater than 50% at 25 μM on day 5 of the study. For this, murine macrophages were cultured in an atmosphere of 5% $CO_2$ and 95% air at 37° C. during 48 hours with the products to assay dissolved in DMSO at three concentrations: 100, 200 and 400 μM. The cellular viability was determined based on the conservation of mitochondrial activity by the MTT/formazan method. This assay included Nifurtimox, Ketoconazole and Terbinafine as reference drugs. Table 2 shows some results by way of example.

TABLE 2

Biological evaluation of non-specific cytotoxicity in J774 murine macrophages.

| Compounds | PC[a] J774 macrophages (%) | | | IC$_{50}$ (μM)[c] |
|---|---|---|---|---|
| | 100 μM[b] | 200 μM[b] | 400 μM[b] | |
| (4-amino imidazo-thiadiazine with benzyl) | 17.6 | 24.3 | 29.4 | >400 |
| (4-amino imidazo-thiadiazine with cyclohexyl) | 1.4 | 8.0 | 11.5 | >400 |
| (4-amino imidazo-thiadiazine with 2-fluorophenyl and N-(4-chlorobenzyl)) | 100.0 | 100.0 | 100.0 | <100 |

TABLE 2-continued

Biological evaluation of non-specific cytotoxicity in J774 murine macrophages.

| Compounds | PC[a] J774 macrophages (%) | | | IC$_{50}$ ($\mu$M)[c] |
|---|---|---|---|---|
| | 100 $\mu$M[b] | 200 $\mu$M[b] | 400 $\mu$M[b] | |
| 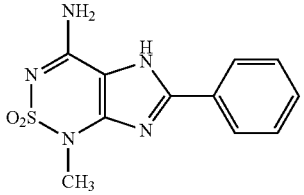 [SMILES: CN1c2nc(-c3ccccc3)[nH]c2C(N)=NS1(=O)=O] | 22.5 | 77.5 | 99.0 | 128.4 |
| Nifurtimox | 1.0 | 13.0 | 90.0 | 316.0 |
| Terbinafine | 10.0 | 26.0 | 60.0 | 339.0 |
| Ketoconazole | 86.0 | 98.0 | 87.0 | <100 |

[a]Percentage of non-specific cytoxicity against J774 murine macrophages.
[b]Concentration of compound assayed.
[c]IC$_{50}$ concentration of compound which reduces the growth of macrophages by 50%. The results are the average of the two independent evaluations with an error less than 3%.

It is clearly observed that the derivatives claimed in the present invention have selectivity towards the cells of the parasite in the order of or better than the reference compounds.

On the other hand, the capacity of inhibiting the cruzipain enzyme was determined in order to study a possible action mechanism of the most active compounds. The capacity of inhibiting the cruzipain enzyme was performed according to the protocol detailed below: cruzipain (10 $\mu$L) was incubated with a reaction mixture containing a final concentration of 50 mM of Tris-HCl buffer solution, pH 7.6, 10 mM $\beta$-mercaptoethanol and 25, 50 or 100 $\mu$M of the inhibitor during 10 min at ambient temperature. Later the chromogenic substrate Bz-Pro-Phe-Arg-p-NA was aggregated at a final concentration of 150 $\mu$M, and the increase in absorbance at 410 nm was followed for 5 min at temperature in a Beckman DU 650 spectrophotometer. The inhibitors were added dissolved in DMSO and the controls (100% of enzymatic activity) contained the same concentration of solvent. The final volume of the assay is 100 $\mu$L. The values represented at least three independent assays. The data obtained for some of the derivatives in table 3 are shown by way of example.

TABLE 3

Cruzipain inhibition results.

| Compounds | % Inhibition CP | | |
|---|---|---|---|
| | 25 $\mu$M | 50 $\mu$M | 100 $\mu$M |
| 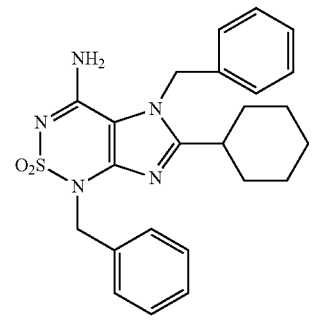 [SMILES: NC1=NS(=O)(=O)N(Cc2ccccc2)c2nc(C3CCCCC3)n(Cc3ccccc3)c21] | 0 | 30 | 58 |

TABLE 3-continued

Cruzipain inhibition results.

| Compounds | % Inhibition CP | | |
|---|---|---|---|
| | 25 $\mu$M | 50 $\mu$M | 100 $\mu$M |
| 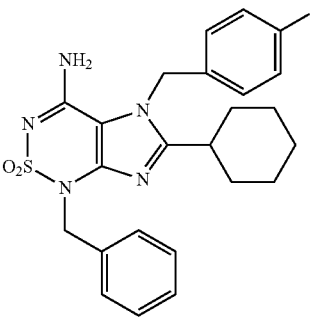 | 10 | 39 | 40 |
| 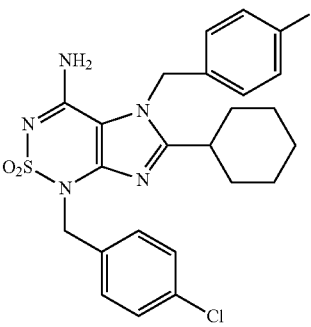 | nd | nd | 31 |

TABLE 3-continued

Cruzipain inhibition results.

| Compounds | % Inhibition CP | | |
|---|---|---|---|
| | 25 μM | 50 μM | 100 μM |
| 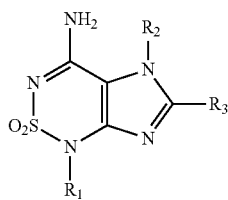 | 0 | 7 | 28 |
| 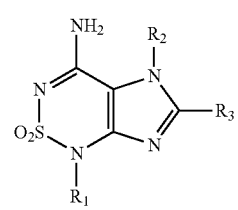 | 7 | 30 | 30 |

This study demonstrates that one of the possible action mechanisms through which the compounds of the invention act as antichagasics is the inhibition of the cruzipain enzyme since this is inhibited in dose-dependent form.

The invention claimed is:

1. A pharmaceutical composition comprising a compound of general formula (I):

(I)

wherein:
$R_1$ and $R_2$ are the same or different, and are selected from the group consisting of hydrogen, alkyl ($C_1$-$C_6$), cycloalkyl, heterocycle, aryl and aralkyl, wherein $R_1$ and/or $R_2$ are benzyl substituted with a halogen group; and
$R_3$ is selected from the group consisting of hydrogen, alkyl ($C_1$-$C_6$), cycloalkyl, heterocycle, aryl, and aralkyl,
or an isomer, pharmaceutically acceptable salt and/or solvate thereof.

2. The compound according to claim 1, wherein $R_1$ or $R_2$ is hydrogen, alkyl ($C_1$-$C_3$) or benzyl.

3. The composition according to claim 1, wherein $R_3$ is alkyl ($C_1$-$C_3$), phenyl, benzyl, phenethyl, cycloalkyl ($C_5$-$C_6$) or heterocycle.

4. The composition according to claim 3, wherein $R_3$ is tetrahydrofuryl, pyridyl, thienyl or furyl.

5. The composition according to claim 3, wherein $R_3$ is phenyl, benzyl or phenethyl substituted with a halogen group.

6. The composition according to claim 1, wherein the halogen group is chlorine or fluorine.

7. The composition according to claim 1, wherein the compound is selected from the group consisting of the compounds of formula:
    4-amino-1-(4-chlorobenzyl)-6-(2-fluorophenyl)-5H-imidazo[4,5-c][1,2,6]thiadiazine 2,2-dioxide,
    4-amino-6-cyclohexyl-1-(4-chlorobenzyl)-5H-imidazo[4,5-c][1,2,6]thiadiazine-2,2-dioxide,
    4-amino-1,5-bis(4-chlorobenzyl)-6-cyclohexylimidazo[4,5-c][1,2,6]thiadiazine-2,2-dioxide,
    4-amino-1-(4-chlorobenzyl)-6-(2-fluorophenyl)-5-(2-naphthyl)imidazo[4,5-c][1,2,6]thiadiazine 2,2-dioxide,
    4-amino-1-benzyl-5-(4-chlorobenzyl)-6-phenylimidazo[4,5-c][1,2,6]thiadiazine-2,2-dioxide and
    4-amino-6-cyclohexyl-5-(4-chlorobenzyl)-1-benzylimidazo[4,5-c][1,2,6]thiadiazine 2,2-dioxide.

8. A method for treatment of parasitic diseases in a subject in need thereof comprising administering to said subject an effective amount of a pharmaceutical composition comprising a compound of general formula (I):

(I)

wherein:
$R_1$ and $R_2$ are the same or different and are selected from the group consisting of hydrogen, alkyl ($C_1$-$C_6$), cycloalkyl, heterocycle, aryl, and aralkyl; and
$R_3$ is selected from the group consisting of hydrogen, alkyl ($C_1$-$C_6$), cycloalkyl, heterocycle, aryl, and aralkyl,
or an isomer, pharmaceutically acceptable salt, and/or solvate thereof, and wherein the parasitic disease is caused by parasites of the genus *Trypanosoma*.

9. The method according to claim 8, wherein the parasitic disease is Chagas disease.

10. The composition according to claim 1, wherein the composition further comprises a pharmaceutically acceptable vehicle.

11. The composition according to claim 10, further comprising a second active principle, wherein the second active principle is not a compound of formula I.

12. A compound selected from the group consisting of formula:
    4-amino-6-(2-fluorophenyl)-1H,5H-imidazo[4,5-c][1,2,6]thiadiazine 2,2-dioxide,
    4-amino-6-(3-pyridyl)-1H,5H-imidazo[4,5-c][1,2,6]thiadiazine 2,2-dioxide,
    4-amino-6-(3-thienyl)-1H,5H-imidazo[4,5-c][1,2,6]thiadiazine 2,2-dioxide,
    4-amino-6-(4-dimethylaminophenyl)-1H,5H-imidazo[4,5-c][1,2,6]thiadiazine-2,2-dioxide,
    4-amino-6-cyclopentyl-1H,5H-imidazo[4,5-c][1,2,6]thiadiazine 2,2-dioxide,
    4-amino-6-cyclohexyl-1H,5H-imidazo[4,5-c][1,2,6]thiadiazine 2,2-dioxide, 4-amino-6-(3-tetrahydrofuryl)-1H,5H-imidazo[4,5-c][1,2,6]thiadiazine 2,2-dioxide, 4-amino-6-ethyl-1H,5H-imidazo[4,5-c][1,2,6]thiadiazine 2,2-dioxide, 4-amino-6-phenethyl-1H,5H-imidazo[4,5-c][1,2,6]thiadiazine 2,2-dioxide, 4-amino-1-(4-chlorobenzyl)-6-(2-fluorophenyl)-5H-imidazo[4,5-c][1,2,6]thiadiazine 2,2-dioxide, 4-amino-6-phenyl-1-methyl-5H-imidazo[4,5-c][1,2,6]thiadiazine 2,2-dioxide, 4-amino-1,5-dibenzyl-6-cyclohexylimidazo[4,5-c][1,2,6]thiadiazine 2,2-dioxide, 4-amino-1,5-dibenzyl-6-phenylimidazo[4,5-c][1,2,6]thiadiazine 2,2-dioxide, 4-amino-6-cyclohexyl-1-(4-chlorobenzyl)-5H-imidazo[4,5-c][1,2,6]thiadiazine-2,2-dioxide 4-amino-1,5-bis(4-chlorobenzyl)-6-cyclohexylimidazo[4,5-c][1,2,6]thiadiazine-2,2-dioxide, 4-amino-1-benzyl-5-(4-chlorobenzyl)-6-phenylimidazo[4,5-c][1,2,6]thiadiazine-2,2-dioxide, 4-amino-6-cyclohexyl-5-(4-chlorobenzyl)-1-benzylimidazo[4,5-c][1,2,6]thiadiazine 2,2-dioxide, and 4-amino-6-(3-thienyl)-1-methyl-5H-imidazo[4,5-c][1,2,6]thiadiazine 2,2-dioxide.

13. The composition according to claim 5, wherein the halogen group is chlorine or fluorine.

14. The method of claim 8, wherein $R_1$ and/or $R_2$ is hydrogen, alkyl ($C_1$-$C_3$), or benzyl.

15. The method of claim 8, wherein $R_1$ and/or $R_2$ are benzyl substituted with a halogen group.

16. The method of claim 8, wherein $R_3$ is alkyl ($C_1$-$C_3$), phenyl, benzyl, phenethyl, cycloalkyl (C5-C6), or heterocycle.

17. The method of claim 16, wherein $R_3$ is tetrahydrofuryl, pyridyl, thienyl, or furyl.

18. The method according to claim 16, wherein $R_3$ is phenyl, benzyl, or phenethyl substituted with a halogen group.

19. The method of claim 15, wherein the halogen group is chlorine or fluorine.

20. The method of claim 9, wherein the compound of general formula (I) is selected from the group consisting of:

4-amino-6-benzyl-1H,5H-imidazo[4,5-c][1,2,6]thiadiazine 2,2-dioxide, 4-amino-6-(5-nitro-2-furyl)-1H,5H-imidazo[4,5-c][1,2,6]thiadiazine 2,2-dioxide, 4-amino-6-(3-pyridyl)-1H,5H-imidazo[4,5-c][1,2,6]thiadiazine 2,2-dioxide, 4-amino-6-(2-fluorophenyl)-1H,5H-imidazo[4,5-c][1,2,6]thiadiazine 2,2-dioxide, 4-amino-6-(3-thienyl)-1H,5H-imidazo[4,5-c][1,2,6]thiadiazine 2,2-dioxide, 4-amino-6-(4-dimethylaminophenyl)-1H,5H-imidazo[4,5-c][1,2,6]thiadiazine 2,2-dioxide, 4-amino-6-cyclopentyl-1H,5H-imidazo[4,5-c][1,2,6]thiadiazine 2,2-dioxide, 4-amino-6-cyclohexyl-1H,5H-imidazo[4,5-c][1,2,6]thiadiazine 2,2-dioxide, 4-amino-6-(3-tetrahydrofuryl)-1H,5H-imidazo[4,5-c][1,2,6]thiadiazine 2,2-dioxide, 4-amino-6-ethyl-1H,5H-imidazo[4,5-c][1,2,6]thiadiazine 2,2-dioxide, 4-amino-6-phenethyl-1H,5H-imidazo[4,5-c][1,2,6]thiadiazine 2,2-dioxide, 4-amino-1-(4-chlorobenzyl)-6-(2-fluorophenyl)-5H-imidazo[4,5-c][1,2,6]thiadiazine 2,2-dioxide, 4-amino-6-phenyl-1-methyl-5H-imidazo[4,5-c][1,2,6]thiadiazine 2,2-dioxide, 4-amino-1,5-dibenzyl-6-cyclohexylimidazo[4,5-c][1,2,6]thiadiazine 2,2-dioxide, 4-amino-1,5-dibenzyl-6-phenylimidazo[4,5-c][1,2,6]thiadiazine 2,2-dioxide, 4-amino-6-cyclohexyl-1-(4-chlorobenzyl)-5H-imidazo[4,5-c][1,2,6]thiadiazine 2,2-dioxide, 4-amino-1,5-bis(4-chlorobenzyl)-6-cyclohexylimidazo[4,5-c][1,2,6]thiadiazine 2,2-dioxide, 4-amino-1-(4-chlorobenzyl)-6-(2-fluorophenyl)-5-(2-naphthyl)imidazo[4,5-c][1,2,6]thiadiazine 2,2-dioxide, 4-amino-6-phenyl-1H,5H-imidazo[4,5-c][1,2,6]thiadiazine 2,2-dioxide, 4-amino-6-methyl-1H,5H-imidazo[4,5-c][1,2,6]thiadiazine 2,2-dioxide, 4-amino-1-benzyl-6-phenyl-5H-imidazo[4,5-c][1,2,6]thiadiazine 2,2-dioxide, 4-amino-1-benzyl-5-(4-chlorobenzyl)-6-phenylimidazo[4,5-c][1,2,6]thiadiazine 2,2-dioxide, 4-amino-6-cyclohexyl-5-(4-chlorobenzyl)-1-benzylimidazo[4,5-c][1,2,6]thiadiazine 2,2-dioxide, and 4-amino-6-(3-thienyl)-1-methyl-5H-imidazo[4,5-c][1,2,6]thiadiazine 2,2-dioxide.

* * * * *